USOO5766890A

United States Patent [19]
Kacian et al.

[11] Patent Number: 5,766,890
[45] Date of Patent: Jun. 16, 1998

[54] KITS FOR SUPPRESSING INHIBITION OF ENZYME-MEDIATED REACTIONS BY IONIC DETERGENTS USING HIGH CONCENTRATIONS OF NON-IONIC DETERGENTS

[75] Inventors: Daniel Louis Kacian; Diane Lisa McAllister, both of San Diego, Calif.

[73] Assignee: Gen-Probe Incorporated, San Diego, Calif.

[21] Appl. No.: 779,341

[22] Filed: Jan. 6, 1997

Related U.S. Application Data

[60] Continuation of Ser. No. 433,991, May 4, 1995, abandoned, which is a division of Ser. No. 212,131, Mar. 10, 1994, abandoned.

[51] Int. Cl.$^6$ ................................................. C12P 19/34
[52] U.S. Cl. ........................ 435/91.2; 435/6; 435/15; 435/810
[58] Field of Search ........................ 435/6, 91.2, 15, 435/810

[56] References Cited

U.S. PATENT DOCUMENTS

| | | | |
|---|---|---|---|
| 5,004,684 | 4/1991 | Simpson et al. | 435/8 |
| 5,175,094 | 12/1992 | Mallonee | 435/69.3 |
| 5,358,690 | 10/1994 | Guirguis | 422/58 |
| 5,538,870 | 7/1996 | Noeth et al. | 435/91.2 |

FOREIGN PATENT DOCUMENTS

| | | |
|---|---|---|
| 0428197 | 5/1991 | European Pat. Off. |
| 0488243 | 6/1992 | European Pat. Off. |
| 0574267 | 6/1992 | European Pat. Off. |
| 9208807 | 5/1992 | WIPO |
| 9426867 | 11/1994 | WIPO |

OTHER PUBLICATIONS

Loeffelholz et al., *J. Clin. Micro.* 30(11), 2847–2851 (1992).

Herman, et al. *Direct Detection of Chlamydia trachomatis in Urogenital Specimens Using a Rapid, PCR-Based Assay System.* Abstract, American Society for Microbiology; Mar., 1991.

Helenius, A. and K. Simons. Solubilization of membranes by detergents. Biochim. Biophys. Acta 415:29–79. Elsevier Scientific Publication Co., Amsterdam (1975).

Ey, P.L. and E. Ferber. Calf thymus alkaline phosphatase II; interactions with detergents. Biochim. Biopys. Acta 480:163–177. Elsevier North–Holland Biomedical Press (1977).

Stralfors, P. Et al. Removal of non–ionic detergent from proteins fractionated by electrofusing. Biochim. Biophys. Acta 533:90–97. Elsevier North–Holland Biomedical Press (1978).

Saito, M. Et al. Action of arthrobacter ureafaciens sialidase on sialglycolipid substrates. J. Biol. Chem. 254(16):7845–54 (1979).

Berge, R. Et al. Variations on the activity of microsomal palmitoyl–CoA hydrolase in mixed micelle solutions of palmitoyl–CoA and non–ionic detergents on the Triton X series. Biochim. Biophys. Acta 666:25–35, Elsevier North–Holland Biomedical Press (1981).

Corti, M. Et al. GMI–Ganglioside–Triton X–100 mixed micelles; changes of micellar properties studied by laser–light scattering and enzymatic methods. Chemistry and Physics of Lipids 28:197–214 (1981).

Wittenburg, C. And E. Tripplett. A detergent–activated tyrosinase from xenopus laevis. J. Biol. Chem. 260(23):12542–12546 (1985).

Tandon, S. And P. Horowitz. Detergent–assisted refolding of guanidinium chloride denatured rhodanese. J. Biol. Chem. 262(10):4486–4491 (1987).

Baselski, V. Et al. Comparison of Roche Chlamydia PCR test to McCoy cell culture in obstetric patients. Dept. of Pathology and Obstet. Gynecology, Univ. Of Tenn., Memphis, TN. Abstract from meeting of the American Society for Microbiology: May 26–30, 1992, Atlanta, GA.

Package insert for brochure of Amplicor's *Chlamydia trachomatis* test manufactured by Roche–Diagnostic Systems, Nutley, New Jersey, Jun. 1993.

Bachmann, et al., "Improvement of PCR amplified DNA sequencing with the aid of detergents", 18(5):1309, (1990).

Gelfand, "Taq DNA Polymerase", PCR Technology—Principles and Applications for DNA Amplification—Stockton Press, Chpt. 2:17–22, (1990).

*Primary Examiner*—Kenneth R. Horlick
*Attorney, Agent, or Firm*—Carlos A. Fisher

[57] ABSTRACT

Methods and kits for the use of a non-ionic detergent to suppress enzyme inhibition in a reaction solution due to the presence of inhibiting ionic detergent. Prior to reaction, the reaction mixture is given an effective amount of a non-ionic detergent, and agitated. The enzyme is then added, and the enzymatic reaction is the allowed to proceed. Also disclosed are preferred embodiments of the present invention, and kits for nucleic acid amplification of a biological sample in the presence of an ionic detergent.

25 Claims, 1 Drawing Sheet

KITS FOR SUPPRESSING INHIBITION OF ENZYME-MEDIATED REACTIONS BY IONIC DETERGENTS USING HIGH CONCENTRATIONS OF NON-IONIC DETERGENTS

This is a file-wrapper continuation application of 08/433,991, filed May 4, 1995, entitled "Method For Suppressing Inhibition Of Enzyme-Mediated Reactions By Ionic Detergents", now abandoned, which is a divisional application of 08/212,131, filed Mar. 10, 1994, entitled "Method For Suppressing Inhibition Of Enzyme-Mediated Reactions By Ionic Detergents," abandoned.

TECHNICAL FIELD OF THE INVENTION

The present invention relates to methods for conducting enzymatic reactions in the presence of ionic detergents, for example lithium lauryl sulphate (LLS) and sodium dodecyl sulfate (SDS), which are often present in diagnostic and clinical samples as solubilizing and protein denaturing agents. This invention thereby eliminates the necessity for lengthy and labor-intensive procedures to separate the detergent from an analyte or an enzyme substrate before initiating the desired reaction. The present invention further relates to a method for conducting enzyme-mediated nucleic acid amplification reactions such as the polymerase chain reaction (PCR) or restriction enzyme digests in the presence of anionic detergents such as LLS without the need for a detergent removal step.

BACKGROUND OF THE INVENTION

This invention concerns enzyme-mediated chemical reactions conducted in vitro, and techniques for preventing their inhibition in the presence of detergents. Detergents are common tools in medical and biological research laboratories, primarily due to their ability to solubilize various proteins, cell wall and membrane components, and other cellular organelles, substructures, and components which are either insoluble or incompletely soluble in aqueous solution alone. Thus, detergents are often components of extraction or lysis buffers, both as lytic agents and as effective inhibitors of undesired enzyme activities such as those contributed by the proteases and nucleases normally present in a crude cell lysate. Additionally, such detergents are often used for the same purposes in the purification of nucleic acids.

Most enzymes used as tools in applied molecular and biological chemistry are quite sensitive to detergents, especially strong ionic detergents such as sodium dodecyl sulphate (SDS) or lithium lauryl sulphate (LLS). Such ionic detergents can bind strongly to proteins, often resulting in irreversible denaturation of the protein. (See American Society for Microbiology, *Manual of Methods for General Bacteriology* 57–58 (1981)). However, for precisely this reason ionic detergents such as LLS are often an extremely valuable and inexpensive short- to medium-term preservative of nucleic acids in solution. Thus, such agents are useful to assist in accomplishing the first step of a nucleic acid hybridization assay using microorganisms; extraction of the nucleic acids from microbial cells or particles. Ionic detergents help to solubilize the cell wall and cell membrane, and to simultaneously prevent degradation of the nucleic acids by nucleases. (See id.) Moreover, strong ionic detergents such as SDS or LLS are often added to the lysis, permeabilization, or transport media in which clinical specimens are conveyed to the laboratory for analysis.

Often nucleic acids obtained from a biological sample are subsequently subjected to enzymatic manipulation, such as digestion with a restriction endonuclease or an exonuclease specific to DNA or RNA. Additionally, nucleic acids obtained from such samples are often not present in amounts large enough for them to be directly detected and/or quantified by nucleic acid hybridization techniques. Thus, the nucleic acid sequences of interest in such samples must normally be enzymatically amplified to be detected.

In biological or clinical samples to be subjected to one or more rounds of nucleic acid amplification or another enzyme-mediated reaction, the detergent must be separated from the nucleic acids in solution before an enzyme can be added to the reaction mixture. Dialysis or ultrafiltration, which usually works well to remove small molecules from a solution will not effectively remove most detergents, probably due both to the size of the micelles formed by the aggregation of the detergent molecules, as well as ionic or hydrophobic binding of the detergent molecules to larger solutes. Moreover, neither dialysis nor ultrafiltration is conveniently adaptable for use in a commercial diagnostic kit.

It would be convenient and cost-effective to perform an enzyme-mediated reaction such as nucleic acid amplification or a restriction digest in the same tube or collection vessel as is used to transport the biological sample to the laboratory for analysis, i.e. in the presence of SDS or LLS. Alternatively, it would be desirable to conduct such a reaction using such a sample as the immediate starting material, rather than having to subject the sample to an additional detergent-removing step. Although SDS can be precipitated with solvents such as acetone, acetone can denature or precipitate some enzymes. Moreover, the desired reaction may be inhibited by traces of acetone or other precipitating agents.

Currently, nucleic acids in a crude sample are generally purified prior to conducting an amplification by means of a phenol/chloroform extraction and subsequent ethanol precipitation. The method of the present invention takes advantage of both the similarities and the differences between ionic and non-ionic detergents to eliminate the necessity for such a step, thereby allowing enzyme-mediated reactions to be performed using nucleic acids in a biological sample, even when the sample contains an amount of ionic detergent which would normally inhibit the reaction.

The present invention is preferably a method for performing a nucleic acid amplification reaction, such as the polymerase chain reaction (PCR) or a transcription-based amplification system, in the presence of anionic detergents such as sodium dodecyl sulphate (SDS) or lithium lauryl sulphate (LLS). However, this present invention should be capable of preventing the inhibition of other enzymatic reactions, such as restriction digests, endo- and exonuclease digests, and kinase and transferase reactions by ionic detergents as well. Nor does the Applicant contemplate that the application of the present invention is limited to enzymatic reactions involving nucleic acids. Thus, while the embodiments of the present invention contained herein illustrate the use of the present invention in amplification reactions, such embodiments are meant to be exemplary only, the scope of the present invention being defined solely by the claims with which this specification concludes.

While not wishing to be bound by theory, Applicants believe that the formation of colloidal aggregates comprising heterogeneous micelles of non-ionic and ionic detergent molecules effectively remove the ionic detergent molecules from solution, thus making them unavailable to bind with or denature the subsequently added enzyme.

The ability of detergents to enhance or restore the activity of some enzymes has been reported. Saito, M., et al., *Action of Arthrobacter ureafaciens Sialidase on Sialoglycolipid Substrates*, 254 *J. Biol. Chem.* 7845–54 (1979). The use of heterogeneous micelles of ionic and non-ionic detergents as a method for the reactivation of detergent-inhibited proteins has also been reported. See Ey, P. L. & Ferber, E., *Calf Thymus Alkaline Phosphatase II. Interaction with Detergents*, 480 *Biochim. Biophys. Acta* 163–77 (1977); Berge, R. K., et al., *Variations in the Activity of Microsomal Palmitoyl-CoA Hydrolase in Mixed Micelle Solutions of Palmitoyl-CoA and Non-Ionic Detergents of the Triton X Series*, 666 *Biochim. Biophys. Acta* 25–35 (1981), Tandon S., & Horowitz, P. M., *Detergent-assisted Refolding of Gaunidinium Chloride-denatured Rhodanese*, 262 *J. Biol. Chem.* 4486–91 (1987). Additionally, the formation of heterogeneous micelles of ionic and non-ionic detergents has been reported as a method for removing inhibiting concentrations of non-ionic detergents from a solubilized enzyme preparation. Stralfors, P. et al., *Removal of Nonionic Detergent from Proteins Fractionated by Electrofocusing*, 533 *Biochim. Biophys. Acta* 90–97 (1978).

All of the methods mentioned in the publications listed above involve the activation or reactivation of enzymes in a detergent solution; none of these methods teach or suggest the formation of heterogeneous micelles in a solution containing an enzyme substrate before the addition of active enzyme. Additionally, in all these cases detergents were used to solubilize, purify, or activate the enzyme; in no case was the detergent initially added to solubilize and stabilize the enzyme substrate rather than the enzyme itself.

DEFINITIONS

In this application the following terms have the following meanings, unless expressly stated to the contrary herein.

By "substantial inhibition" and "substantially inhibit" is meant a decrease in enzyme activity below that acceptable for reliable, sensitive and reproducible assays of enzyme activity.

By "target nucleic acid sequence", "target nucleotide sequence" or "target sequence" is meant a specific nucleic acid sequence, or the nucleic acid sequence complementary thereto.

By "heterogeneous micelles" is meant hydrophobic aggregates comprising monomers of ionic and non-ionic detergent molecules in a liquid medium.

By "mixed micelles" is meant "heterogeneous micelles", as defined in this disclosure.

By "complementary" is meant having a nucleic acid sequence whereby stable hydrogen bonds are formed between the nucleotide bases of a region of one nucleic acid strand and those of a region of another nucleic acid strand under conditions suitable for discriminatory nucleic acid hybridization. That is, hydrogen bonds are most commonly formed between an adenosine(A) residue on one strand and a thymine(T) or uracil(U) residue on another strand, and between a guanine(G) residue on one strand and a cytosine (C) residue on another strand. Such regions of complementarily generally involve between about 12 and 100 or more contiguous nucleotides of each nucleic acid strand.

By "sufficiently complementary" is meant capable of forming a double-stranded hydrogen-bonded region with a target nucleic acid under hybridization conditions suitable to prevent a non-complementary nucleic acid from hybridizing thereto. While two nucleic acid strands are sufficiently complementary if they have 100% complementarily over specific contiguous and corresponding regions, it is known to those skilled in the art that two single stranded nucleic acids having regions of less than 100% complementarily can form a double-stranded region under selective hybridization conditions. Such regions, not 100% complementary but able to form stable double stranded regions under these hybridization conditions, are hereby considered sufficiently complementary.

By "analogous" is meant a single-stranded nucleic acid region having a nucleotide sequence identical or similar to that of a second single-stranded nucleic acid to which it is being compared. This includes, for example, nucleic acids wherein the first nucleic acid contains a uracil residue in said region in place of a thymine present in the second nucleic acid and nucleic acid regions encoding or comprising functionally similar or identical biological agents or parts thereof.

By "sufficiently analogous" is meant having a nucleic acid sequence, as compared to a first single stranded nucleic acid, which allows a second single-stranded nucleic acid having that sequence to form a stable, hydrogen-bonded double-stranded region with a third nucleic acid under nucleic acid hybridization conditions, and wherein the third nucleic acid is sufficiently complementary to the first nucleic acid.

By "RNAse-inhibiting agent" is meant any agent capable of preventing the degradation of RNA by enzymes having RNAse activity. The term includes but is not limited to: enzymes such as proteases, cross-linking reagents, antibodies, and compounds which block the active site of the RNAse molecule.

By "nucleic acid" is meant polydeoxyribonucleotides or polyribonucleotides of at least two, and preferably 10 or more nucleotides in length. The term "nucleic acid" includes polynucleotides, oligonucleotides, and DNA or RNA molecules. The term "nucleic acid" can refer to either single-stranded or double-stranded polynucleotides, or both.

By "target nucleic acid" is meant a nucleic acid comprising a target nucleic acid sequence.

By "biological sample" or "test sample" is meant any specimen or sample containing substances derived at any time from living organisms containing nucleic acids. Such samples include, but are not limited to, food or agricultural samples; environmental samples; samples containing body fluids, secretions or excretions such as urine, blood, milk, cerebrospinal fluid, sputum, saliva, stool, lung aspirates, tears, lymphatic fluid, or semen; throat or genital swabs; and bacterial, viral, plant or animal cell cultures, suspensions or lysates.

By "amplification" or "target amplification" is meant increasing the number of target nucleic acid molecules having a target nucleic acid sequence.

Methods for detecting nucleic acids are well known in the art, and generally consist of contacting at least one labeled single-stranded nucleic acid probe with a single-stranded target nucleic acid under hybridization conditions, where the probe has a nucleic acid sequence sufficiently complementary to that of the target nucleic acid and the target nucleic acid has a specific sequence the presence of which is desired to be known; such methods are described in Maniatis, T., et al., *Molecular Cloning: A Laboratory Manual* (Cold Springs Harbor Laboratory 1982). Detection of double-stranded hybrid molecules depends on the nature of the label used; generally the probe incorporates a radioactive isotope such as $^{32}P$, $^{3}H$, or $^{14}C$, or is conjugated with a fluorescent moiety, a hapten, or another non-radioactive reporter group. See e.g., Maniatis, supra, and Arnold et al., PCT US88/02746, both of which are hereby incorporated by reference as part of this disclosure.

The sensitivity and reliability of diagnostic nucleic acid hybridization can be improved by using any one of a number of enzyme-mediated amplification systems to increase the copy number of the target nucleic acid sequence. Generally, such methods use the target nucleic acid as a template for at least one nucleic acid polymerase which may be used in concert with two or more nucleic acid primers in reiterative cycles to provide an exponential increase in the number of target nucleic acid sequences. Examples of amplification systems that are well known to those skilled in the art include the polymerase chain reaction (PCR) (Mullis et al., 155 Methods in Enzymology 335–50 (1987) and use of the double-stranded PCR products as templates for making multiple single-stranded RNA transcripts (Murakawa et al., 7 DNA 287–95 (1988)). Other amplification systems involve alternate rounds of DNA synthesis on an RNA template and transcription to amplify the target sequence. See e.g., Burg et al., WO 89/1050; Gingeras et al., WO 88/10315; Kacian and Fultz, EPO Application No. 89313, both of which are incorporated by reference as part of this disclosure. The preceding list is not intended to be an exhaustive listing of the various amplification methods, and other nucleic acid polymerases suitable for use in a nucleic acid amplification system are known to those skilled in the art. Following amplification, the resulting amplified nucleic acids can then be identified using a detection system as mentioned above.

Thus in a first aspect, the present method features a method for preventing an ionic detergent from denaturing or otherwise substantially inhibiting the activity of enzymes used in nucleic acid amplification reactions comprising: 1) target nucleic acids, 2) one or more nucleic acid primers, each one sufficiently complementary to a common target nucleic acid sequence to form double-stranded hydrogen-bonded regions with the target under suitably selective hybridization conditions, 3) necessary nucleoside triphosphates, salts, and other components necessary to achieve amplification, and 4) a quantity of an ionic detergent. The method of the present invention does not require a detergent removal step such as dialysis or chromatography. The method involves the addition of a non-ionic detergent to the sample and agitation of the sample in order to form mixed micelles of ionic and non-ionic detergent molecules. Following the formation of heterogeneous micelles, the nucleic acid polymerase and any other enzymes needed to conduct amplification can be added to the sample and the nucleic acid amplification reaction performed as usual.

In a second aspect of the present invention, a biological sample containing microorganisms or nucleic acids is contacted with a lysis or extraction buffer, and the released nucleic acids are stored in a buffer containing an ionic detergent such as LLS or SDS for subsequent amplification and use in a nucleic acid detection assay. Prior to the amplification step, a quantity of a non-ionic detergent is added to the extracted nucleic acid mixture either simultaneously with or preceding the addition of an effective quantity of ribo- or deoxyribonucleotide triphosphates, generally two or more nucleic acid primers, and any co-factors or metal ions necessary for the enzymatic reaction. The solution is then mixed vigorously, after which a nucleic acid polymerase is added to the mixture. The reaction mixture is incubated as appropriate for the amplification method used, for example a thermocycling or an isothermal amplification protocol. See e.g., American Society for Microbiology, *Diagnostic Molecular Microbiology: Principles and Applications* 56–70 (1993), which is hereby incorporated by reference. The amplified target nucleic acids are then detected by hybridization methods as described above.

In another aspect, the method of the present invention may be used to prevent the inhibition of other enzymes commonly used in industry, medical clinics, research laboratories and commercial formulations. For example, the method of the present invention may be used to prevent the inhibition of a restriction enzyme digestion of a nucleic acid in a sample containing an anionic detergent without the need to remove the anionic detergent from solution first.

While the foregoing disclosure describes the problem solved by the present invention and its general means of solution, it will be understood that the foregoing disclosure does not in any way limit the present invention or its application, which are defined solely by the claims which follow this disclosure.

SUMMARY OF THE INVENTION

Figure 1:
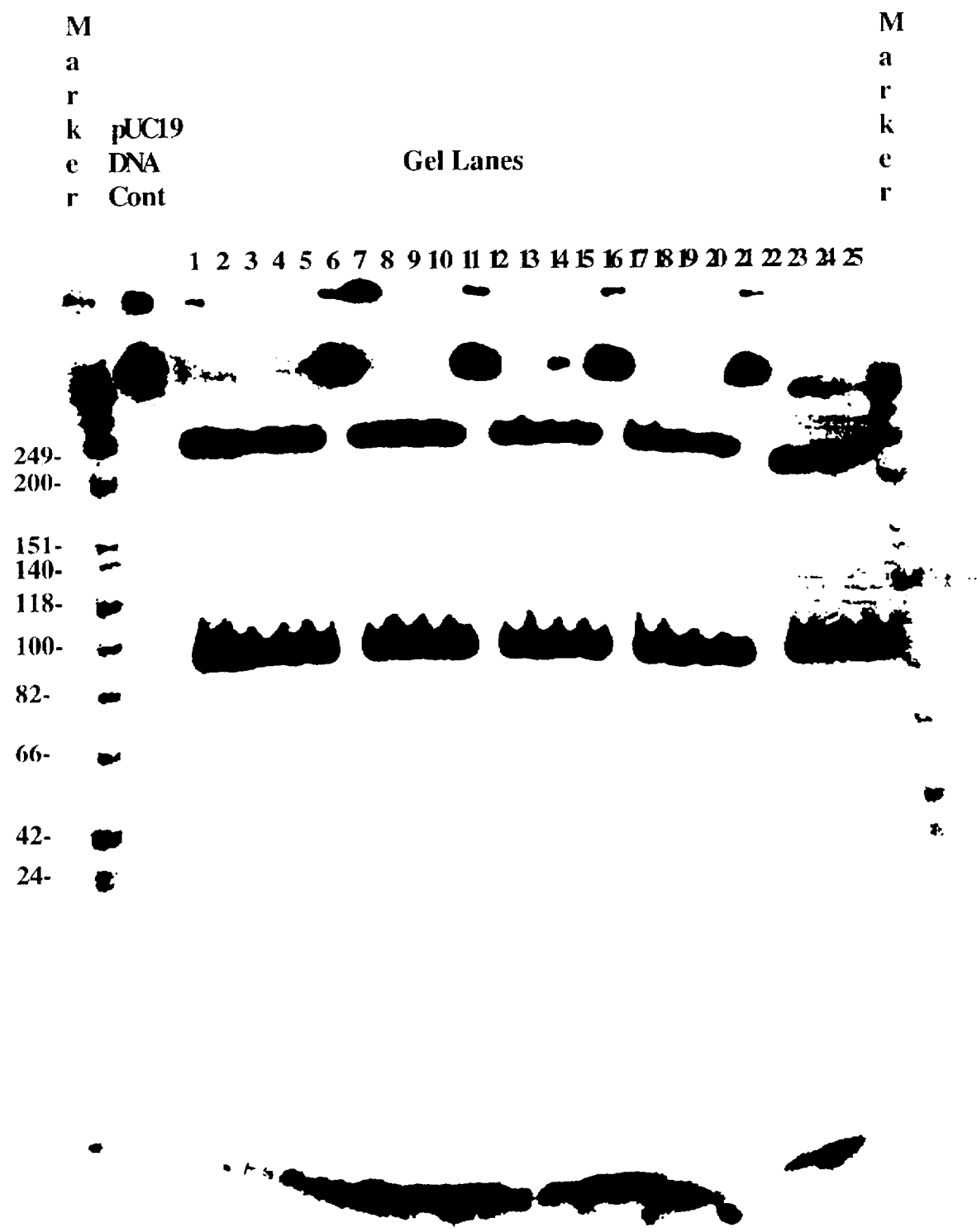
FIG. 1 is an autoradiogram of a 7% polyacrylamide gel on which radiolabeled DNA in samples containing various combinations of ionic and non-ionic detergent were subjected to restriction digestion with restriction endonuclease Pvu II followed by polyacrylamide gel electrophoresis.

The present invention features a method for conducting a enzymatic reaction in a solution containing an ionic detergent, such as sodium dodecyl sulphate (SDS) or lithium lauryl sulphate (LLS), at a concentration which is normally sufficient to inhibit the activity of the enzyme. In one embodiment, the present invention relates to a method for preventing the inhibition of at least one enzyme in a nucleic acid target amplification reaction. The method concerns the addition to a solution containing an anionic detergent (preferably SDS or LLS) and nucleic acids to be analyzed; of, generally, two or more different oligonucleotide primers; one primer having a sequence sufficiently complementary and the other a sequence sufficiently analogous to a target nucleic acid sequence; four different nucleotides; necessary salts and cofactors such as MgCl, or NaCl; and an amount, preferably between 8–20% (v/v), of a non-ionic detergent, preferably polyoxyethylene (20) sorbitan monoalkylates (the Tween series of detergents) or polyoxyethylene p-t-octyl phenol derivatives (e.g., Triton X-100 and Triton X-102). These constituents are mixed, and a nucleic acid polymerase, preferably a heat-stable DNA polymerase such as the DNA polymerase from the bacterium *Thermus aquaticus* (Taq DNA polymerase), is added to the reaction mixture and the mixture is subjected to a nucleic acid amplification procedure, preferably the polymerase chain reaction (PCR). In another preferred embodiment two enzymes are used in the amplification reaction: a reverse transcriptase having RNAse H activity, such as MMLV RT, and a RNA polymerase, such as T7 polymerase.

In another preferred embodiment, the method of the present invention is used to prevent inhibition of a restriction enzyme in the presence of sodium dodecyl sulfate (SDS). Plasmid pUC19 (Bethesda Research Laboratories, Gaithersburg, Md.) was digested with restriction endonuclease Eco R1 at the single Eco R1 site. Following linearization, the plasmid DNA was radiolabeled with [α]-$^{32}$P DATP using the Klenow fragment of *E. coli* DNA polymerase I. The radiolabeled probe was precipitated and resuspended in a solution containing differing amounts of SDS and Tween-20. The DNA was then given an excess of restriction endonuclease Pvu II, and incubated for one hour at 37° C. The resulting samples were analyzed on a 7% polyacrylamide gel under non-denaturing conditions.

Although hydrophobic relationships probably play an important role in the deinhibition of the enzymatic reactions by removing enzyme-inhibiting ionic detergents from solution, micelle formation alone may not be the only determinant as to the suitability of a particular non-ionic detergent in the method described herein. Thus, while the formation of mixed micelles is thought by the Applicants to be important in the practice of this invention, the Applicants remain uncertain as to the precise mechanism which allows enzyme activity to be preserved in the presence of ionic detergent.

It is an object of the present invention to provide a method for conducting a target amplification reaction in the presence of normally inhibiting or denaturing amounts of an ionic detergent such as LLS or SDS.

It is also an object of the present invention to provide a method for conducting a qualitative and/or a quantitative analysis of a biological or clinical sample containing nucleic acids and an ionic detergent such as LLS or SDS, wherein such an analysis involves at least one enzyme-mediated reaction, such as the amplification of a specific nucleic acid sequence or a restriction digest, without the need to separate the nucleic acid analyte from the ionic detergent before commencing the reaction.

It is another object of the present invention to provide a method for preventing the inhibition of a nucleic acid amplification reaction in a test sample wherein the sample includes: 1) nucleic acids to be tested for the presence or absence of a specific nucleic acid sequence; and 2) from about 0.1–1.5% of an ionic detergent, preferably about 0.3–0.7% SDS or LLS, and where the enzyme or enzymes to be employed in the nucleic acid amplification reaction are preferably Taq DNA polymerase, T7 DNA polymerase, and/or retroviral RNA-directed DNA polymerase (reverse transcriptase or RT); most preferably Taq DNA polymerase. The method comprises the steps of a adding non-ionic detergent, preferably between about 8–20% of polyoxyethylene (20) sorbitan monolaurate (Tween-20) or polyoxyethylene (9) p-t-octyl phenol (Triton X-100) to the nucleic acids and ionic detergent, mixing the solution together vigorously to form heterogeneous detergent micelles, adding an effective amount of a nucleic acid polymerase, preferably between about 2–8 units of Taq DNA polymerase and subjecting the reaction mixture to a nucleic acid amplification procedure, such as PCR.

It is further an object of this invention to provide a kit for either the qualitative analysis or quantitative analysis, or both, of biological samples containing nucleic acids or microorganisms which contain nucleic acids. When the sample contains microorganisms, such a kit should provide a lysis, permeabilization, or sample transport reagent including between about 0.1%–1.5% of an ionic detergent, preferably SDS or LLS, to inhibit protease and nuclease activity and to assist in dissolution of the cell wall and membrane. In such a reagent, the liberated nucleic acids are protected from nuclease degradation by the ionic detergent. The kit should also provide a second reagent containing: 1) generally two or more nucleic acid primers having nucleic acid sequences sufficiently complementary to that of a target nucleic acid sequence to form, under hybridization conditions, a hydrogen-bonded region with either or both of the complementary nucleic acid strands having such a target sequence; 2) from about 0.5–10 mM $MgCl_2$ or $MnCl_2$; 3) an effective amount of a disulfide cleaving agent, preferably from about 05–10 mM dithiothreitol (DTT); and 4) from 8 to 20% (v/v) of a non-ionic detergent, preferably polyoxyethylene (20) sorbitan monolaurate (Tween-20) or polyoxyethylene (20) sorbitan monooleate (Tween-80). An aliquot of the sample solution containing the liberated nucleic acids in the lysis, permeabilization or transport medium is added to the second solution, and mixed vigorously. From about 2–8 units of at least one nucleic acid polymerase, preferably Taq DNA polymerase, is then added to the reaction mixture and the mixture is treated according to the normal procedure for the polymerase chain reaction. Following this, the sample is tested for the presence or absence of at least one specific nucleic acid sequence using nucleic acid hybridization methods and a labeled nucleic acid probe.

It is yet another object of the present invention to provide a method for the amplification of nucleic acids in the presence of a ionic detergent, preferably about 0.3 to 0.7% LLS. In this method, the final composition of the starting solution includes the following: 1) about 50 mM Tris-HCl (pH 7.6), 17.5 mM $MgCl_2$, 25 mM KCl and 2 mM spermidine, 2) about 25 mM each of four different ribonucleotide triphosphates (A,U,G and C) and four different deoxyribonucleotide triphosphates (A,T,G and C), 3) about 1 mM DTT, 4) about 20 picomoles of, generally, two or more single-stranded nucleic acid primers which have nucleic acid sequences sufficiently complementary to that of a target nucleic acid sequence to form a double-stranded, hydrogen-bonded region with either a positive or a negative sense nucleic acid strand having such a target nucleic acid sequence, or both, under hybridization conditions. 5) between about $6\times10^{-3}$ to $6\times10^{-9}$ picomoles of a nucleic acid having at least one copy of a specific target nucleic acid sequence.

DETAILED DESCRIPTION OF THE PREFERRED EMBODIMENTS

The claimed method and kit feature a series of steps for conducting a target amplification reaction in the presence of an ionic detergent, as well as a combination of reagents for accomplishing such steps.

In one of its preferred embodiments the present invention provides a method and means for conducting a nucleic acid amplification reaction when the sample to be analyzed contains ionic detergents. The method involves adding a quantity of a non-ionic detergent to the sample solution and mixing the ionic and the non-ionic detergents together vigorously before the addition of the enzyme or enzymes and initiation of the amplification reaction.

While the Applicants used purified nucleic acids in some of their embodiments, any source of nucleic acids, either purified or unpurified can be used so long as it is contains or is suspected of containing the target nucleic acid sequence. This sequence may be present in DNA or RNA, which may be single-stranded or double-stranded. A mixture of these nucleic acids may be used, as may the nucleic acids from a previous amplification reaction. This invention is therefore a generally useful method for overcoming the inhibitory effects of a detergent in a sample containing nucleic acids to be analyzed.

Materials

The non-ionic detergents Tween-20, Tween-40, Tween-80, Triton X-100 and Triton X-102 were purchased from the Sigma Chemical Co., St. Louis, Mo.

The nucleic acid primers were synthesized by use of standard phosphoroamidite chemistry; various such methods are well known in the art, see e.g., Carruthers et al., 154 *Methods in Enzymology* 287 (1987); Bhatt, U.S. Ser. No. 07/319,570 (filed Mar. 6, 1989), and Klem et al., PCT WO92/07864, which are hereby incorporated by reference as part of this disclosure. Applicants prepare the probes using a Model 380A DNA synthesizer (Applied Biosystems, Inc., Foster City, Calif.).

Detection Method

The amplification products were quantified using a detectable chemiluminescent acridinium ester-labeled nucleic acid probe that hybridizes to the target sequence. In particular, a double-stranded hybrid molecule is detected by contacting the amplified sample with the labeled probe under specified hybridization conditions, selectively hydrolyzing the acridinium ester bound to unhybridized probe, and measuring the chemiluminescence of the remaining acridinium ester (i.e. that associated with double-stranded nucleic acid regions) in a luminometer. See e.g., Arnold et al., PCT US88/02746 and Nelson et al., in *Nonisotopic DNA Probe Techniques* 275 (Academic Press, San Diego 1992), which are hereby incorporated by reference.

The following examples do not necessarily represent optimal conditions for the use of the present invention; they are intended to be exemplary only and represent currently preferred embodiments of the present invention. These examples are not intended to be limiting as to the scope of possible embodiments of the claimed method, such embodiments being immediately apparent to those of skill in the art upon exposure to the present disclosure.

EXAMPLE 1

This example demonstrates the effectiveness of using the present method in a transcription-based amplification system, see Kacian & Fultz, supra. The target nucleic acid for this example was a solution of total ribosomal RNA purified from *Ureaplasma urealyticum* (0.6 picomoles/ml) in a buffer containing 30 mM sodium phosphate pH (6.7), 1.0 mM disodium EDTA (ethylenediaminetetracetic acid disodium), 1 mM EGTA (ethylene glycol-bis (β-aminoethyl ether) N,N,N',N'-tetracetic acid), and 110 mM (3.0% w/v) LLS. Serial dilutions were made in the same buffer.

A solution of 25% (v/v) Triton X-102 in deionized water was prepared. Reaction volumes were 100 µl, and reaction was conducted in microcentrifuge tubes. Each tube was given 10 µl of a buffer containing 500 mM Tris-HCl (pH 7.6), 175 mM $MgCl_2$, 250 mM KCL, and 20 mM spermidine, 0.5 µl of 1M DTT, 10 µl of a solution of ribonucleotides containing 25 mM rCTP and rUTP and 65 mM rATP and rGTP, 2 µl of a solution containing 100 mM each of DATP, dTTP, dCTP, and dGTP, 8.6 µl of a solution of 30 pM of the first primer (81(−); SEQ ID NO: 1), 3.4 µl of a solution of 30 pM of the second primer (uur C 1(+); SEQ ID NO: 2), 10 µl of undiluted, 1:10 diluted, or 1:100 diluted target rRNA prepared as described above, varying amounts of the 25% (v/v) Triton X-102 solution, and water to a volume of 93.6 µl. The sequences of these primers are as follows:

SEQ ID NO 1

5'-AATTTAATACGACTCACTATAGG-
GAGAGCGTAGCGATGACCTATTTTACTTGC-3'

SEQ ID NO 2

5'-TGTAGTGATCATATCAGAGTGG-3'

Each reaction tube was mixed vigorously using a vortex mixer, and then the samples were heated to 95° C. for 2 minutes and cooled to room temperature. Moloney Murine Leukemia Virus RNA-directed DNA polymerase (MMLV reverse transcriptase, 300 units) and 400 units of T7 RNA polymerase were separately added to each tube in a total volume of 6.44 µl. The samples were then incubated at 37° C. for 4 hours. Tubes were cooled to 4° C. awaiting the detection step.

Quantification of amplified target sequences was performed according to the HPA chemiluminescence method referred to above and incorporated by reference as part of this disclosure. See Arnold et al., supra. One of two labeled probes specific to the target sequence were used in the hybridization assay. Their sequences are as follows:

SEQ ID NO: 3

5'-GTGATCATATCAGAGTGGAAATACCTGTTCCCATCC-3'

SEQ ID NO: 4

5'-GCTTGTGTCTTCAGTTCGTGAGATCTCGGC-3'

EXAMPLE 2

This example demonstrates the ability of a polyoxyethylene(9) p-t-octyl phenol deriviative (Triton X-102) to act as the non-polar detergent in the method of the present invention. The concentration of LLS was 0.3% (w/v) Triton X-102 concentrations were 9%, 10%, and 11% (v/v) Duplicate experiments were run for each condition, and duplicate HPA detections made for each experiment; the resulting values were averaged. Amount of amplification is proportional to the amount of label detected; this quantity is given in RLU or relative light units. Values appearing in parentheses were control experiments. The results of the amplification experiments are shown below in Table 1.

TABLE 1

Amplification Reaction in Presence of 0.3% (w/v) LLS and Triton X-102
[Average Relative Light Units (RLU)]

| | Input Target RNA (picomoles) | | |
|---|---|---|---|
| | $6 \times 10^{-3}$ | $6 \times 10^{-4}$ | $6 \times 10^{-5}$ |
| No LLS, no Triton X-102 | $(5.2 \times 10^7)$ | | |
| No Target RNA | (100) | | |
| 10% Triton X-102; no LLS | $(1.7 \times 10^8)$ | | |
| 9% Triton X-102 | 24,000 | 770 | 530 |
| 10% Triton X-102 | 72,000 | 280 | 100 |
| 11% Triton X-102 | 78,000 | 87,000 | 87,000 |

EXAMPLE 3

The following experiment demonstrates the sensitivity of nucleic acid amplification according to the presently claimed method. The experiment was conducted as in Example 1, with the following exceptions. Tween-20 was substituted for Triton X-102, and the amounts of added target RNA were $6 \times 10^{-3}$, $6 \times 10^{-5}$, $6 \times 10^{-7}$ and $6 \times 10^{-9}$ picomoles. Final concentrations of Tween-20 were 13, 15 and 20% (v/v) . The results are shown in Table 2.

TABLE 2

Sensitivity of Amplification Reaction in Presence of 0.3% (w/v) LLS and 20% (v/v) Tween-20 [Average Relative Light Units (RLU)]

| | Input Target RNA (picomoles) | | | |
|---|---|---|---|---|
| | $6 \times 10^{-3}$ | $6 \times 10^{-4}$ | $6 \times 10^{-5}$ | $6 \times 10^{-9}$ |
| No LLS, no Tween-20 | | $2.3 \times 10^6$ | $2.3 \times 10^6$ | $2.2 \times 10^6$ |
| LLS, Tween; no target | (6,300) | | | |
| 13% Tween-20 | $2.4 \times 10^6$ | $1.9 \times 10^6$ | $1.3 \times 10^6$ | $1.2 \times 10^6$ |
| 15% Tween-20 | $2.3 \times 10^6$ | $2.2 \times 10^6$ | $1.2 \times 10^6$ | 940,000 |
| 20% Tween-20 | $2.3 \times 10^6$ | $1.6 \times 10^6$ | 310,000 | 320,000 |

EXAMPLE 4

This example demonstrates the effectiveness of the present method for use with nucleic acid amplification employing the polymerase chain reaction (PCR). For this experiment the target nucleic acid was a restriction fragment having a known DNA sequence obtained from a plasmid containing the E6 gene of Human Papilloma Virus. The two oligonucleotide primers (SEQ ID NO: 4 AND SEQ ID NO: 5) were designed to be complementary to opposite strands of the double-stranded target nucleic acid. The sequences of these primers are as follows:

SEQ ID NO: 5

5'-GCAATGTAGGTGTATCTCC-3'

SEQ ID NO: 6

5'-TATGCACAGAGCTGCA-3'

The final reaction volume for each sample was 100 μl. In this experiment, 2 drops of mineral oil were added to each tube, followed by a precalculated amount of water. One microliter of target DNA in 100 mM Tris-HCl pH 7.6, 10 mM EDTA ($1 \times 10^4$ copies of the target sequence) was then added. A buffer containing 30 mM sodium phosphate pH 6.7, 1.0 mM disodium EDTA, 1 mM EGTA, and 110 mM (3.0% w/v) LLS was added to some tubes to give a final LLS concentration of 0.3%. Differing volumes of a 50% (v/v) solution of Tween-20 was also added to some tubes to give a reaction concentration of 10%, 12%, 14%, 16%, 18%, 20%, 22%, or 24%. Following the addition of detergent the samples were mixed on a vortex mixer.

A PCR premix was made separately, containing 10 μl of 10× PCR buffer, 20 nanomoles of each deoxyribonucleotide, 100 picomoles of each nucleic acid primer and 2.5 units of Taq DNA polymerase for each reaction tube. The sample tubes were placed on ice, and the PCR premix was added to each sample and mixed. Each sample was heated to 94° C. for 3 minutes, then taken through 35 thermocycles comprising the following: incubation at 51° C. for 30 seconds, followed by incubation at 72° C. for 2 minutes, and finally at 94° C. for 1 minute. Following the final 94° C. incubation, the samples were incubated at 72° C. for 5 minutes then stored at 4° C. overnight for detection.

Detection was carried out as in Example 1 using a probe complementary to the target nucleic acid sequence. The sequence of the probe is as follows:

SEQ ID NO: 7

5'-GAACAGCAATACAACAAACCGTTGTGTG-3'

The results are shown in Table 3.

TABLE 3

PCR Amplification in the Presence of 0.3% (w/v) LLS

| | Average RLU |
|---|---|
| No LLS, no Tween | 290,000 |
| 10% Tween-20 | 310,000 |
| 12% Tween-20 | 250,000 |
| 14% Tween-20 | 360,000 |
| 16% Tween-20 | 160,000 |
| 19% Tween-20 | 320,000 |
| 20% Tween-20 | 180,000 |
| 22% Tween-20 | 120,000 |
| 24% Tween-20 | 140,000 |

EXAMPLE 5

This experiment shows the effectiveness of Tween-20 to prevent the inhibition of Taq DNA polymerase-mediated PCR at different concentrations of LLS and Tween-20. The experiment was conducted as in Example 3, except as follows: LLS concentrations were made 0%, 0.3%, 0.5%, and 0.7% (w/v). Tween-20 concentrations were variously 0%, 10%, 14%, 18%, and 20% (v/v). The results are shown in Table 4.

TABLE 4

PCR Amplification in Presence of Various Concentrations of LLS and Tween-20 [Average RLU]

| | 0% LLS | 0.3% LLS | 0.5% LLS | 0.7% LLS |
|---|---|---|---|---|
| 0% Tween-20 | 410,000 | 14 | 25 | 45 |
| 10% Tween-20 | 120,000 | 11,000 | 290 | 300 |
| 14% Tween-20 | 170,000 | 170,000 | 64,000 | 280 |
| 18% Tween-20 | 230,000 | 210,000 | 77,000 | 340 |
| 20% Tween-20 | 170,000 | 190,000 | 42,000 | 310 |

EXAMPLE 6

This experiment was performed as is Example 4, except Tween-40 (polyoxyethylene (20) sorbitan monopalmitate) was substituted for Tween-20. The results are shown in Table 5.

TABLE 5

PCR Amplification in Presence of Various Concentrations of LLS and Tween-40 [Average RLU]

| | 0% LLS | 0.3% LLS | 0.5% LLS | 0.7% LLS |
|---|---|---|---|---|
| 0% Tween-40 | 2,500,000 | 48,000 | 4,900 | 5,100 |
| 10% Tween-40 | 160,000 | 260,000 | 5,400 | 5,100 |
| 14% Tween-40 | 180,000 | 110,000 | 65,000 | 5,200 |
| 18% Tween-40 | 150,000 | 82,000 | 52,000 | 17,000 |
| 20% Tween-40 | 77,000 | 49,000 | 32,000 | 6,800 |

EXAMPLE 7

This experiment was conducted as in Example 4, except Tween-80 (polyoxyethylene (20) sorbitan monooleate) was substituted for Tween-20. Experimental compositions which were not tested are indicated "ND". The results are shown in Table 6.

TABLE 6

PCR Amplification in Presence of Various Concentrations of LLS and Tween-80 [Average RLU]

|  | 0% LLS | 0.3% LLS | 0.5% LLS | 0.7% LLS |
|---|---|---|---|---|
| 0% Tween-80 | 2,500,000 | ND | 0.0 | ND |
| 10% Tween-80 | 2,200,000 | 61,000 | 1,100,000 | 230,000 |
| 14% Tween-80 | 690,000 | 260,000 | 130,000 | 0.0 |
| 18% Tween-80 | 900,000 | 750,000 | 140,000 | 94 |
| 20% Tween-80 | 330,000 | 460,000 | 39,000 | 260,000 |

EXAMPLE 8

This experiment demonstrates the effectiveness of the present method for use with biological samples suspected of containing nucleic acids or nucleic acid-containing microorganisms. The sample was a pool of endo-cervical swab specimens in a buffer containing 30 mM sodium phosphate (pH 6.8), 1.0 mM disodium EDTA (ethylenediaminetetracetic acid disodium), 1 mM EGTA (ethylene glycol-bis (β-aminoethyl ether) N,N,N',N'-tetracetic acid), and 110 mM (3.0% w/v) LLS which tested positive for *Chlamydia trachomatis* in a previous direct nucleic acid hybridization assay without amplification.

The samples were treated with 40 μl of a Proteinase K solution (0.1 unit/μl) for each 800 μl of sample, and incubated at 60° C. for 20 minutes. Tween-80 (polyoxyethylene (20) sorbitan monooleate) was added to a sample dilution buffer containing 40 mM Tris-HCl (pH 8.0), 10 mM N-acetyl-L-cysteine (NALC), and 2 mM EDTA. Amounts of Tween-80 were added to this buffer in order to make the final Tween concentration during the amplification 6.4%, 6.8%, 7.2%, 7.6%, 8%, 10% and 12%. Ten microliters of the specimen sample was combined with 40 μl of each concentration of non-ionic detergent in dilution buffer and mixed vigorously using a vortex mixer, then stored for either 3–4 days at 4° C.

25 μl of an amplification buffer containing 20% (w/v) polyvinylpyrrolidone, 16 mM each of rCTP, rATP and rUTP and 20 mM rGTP, 6 mM deoxyribonucleotides, 160 mM Tris pH 7.5, 92 mM MgCl$_2$, 92 mM KCl, 3.0 picomoles of a first primer (T7 AproCtrB(−) 1519; SEQ ID NO: 7) and 25.0 picomoles of a second primer (CtrB(+)1428b; SEQ ID NO: 8) was pipetted into a separate tube for each experiment, and 200 μl of mineral oil was layered on top of each tube. One of the oligonucleotide primers had a nucleic acid sequence analogous to for a region of *Chlamydia trachomatis* ribosomal RNA; the other oligonucleotide primer had a nucleic acid sequence complementary to a region of *Chlamydia trachomatis* ribosomal RNA. The sequences of these primers are as follows:

SEQ ID NO: 8

5'-AATTTAATACGACTCACTATAGGGAGAC-
CCGAAGATTCCCCTTGATCGC-3'

SEQ ID NO: 9

5'-CGGAGTAAGTTAAGCACGCGGACGATTGGAAGA-3'

The 50 μl containing each sample and detergent combination was pipetted through the layered mineral oil into the amplification buffer. Each tube was heated at 95° C. for 5 minutes in a heating block, then transferred to a 42° C. heating block for another 5 minutes before the addition of enzyme. Twenty-five microliters of an enzyme solution containing 900 units Moloney Murine Leukemia Virus reverse transcriptase (MMLV RT) and 400 units T7 RNA polymerase was added to each tube and mixed into solution. Each tube was then incubated for 42° C. for 1 hour, then treated with 20 μl of a solution containing 50 units of essentially RNase-free DNase and 0.1 mM phenylmethylsulfonyl fluoride (PMSF) in ethanol. Samples were incubated for another 10 minutes at 42° C. and HPA detection was carried out as described above using a labeled oligonucleotide probe specific for the target *Chlamydia trachomatis* ribosomal RNA. The sequence of the probe is as follows:

SEQ ID NO: 10

5'-AGAGTCCGTAGAGCGATGAGAACG-3'

Positive controls are indicated in parentheses, and were samples in which the indicated amount of RNA, not contained in a biological sample and in a final concentration of 0.3% LLS, was subjected to the amplification procedure. Each experimental sample was run in duplicate. The results are indicated in the Table 7.

TABLE 7

Amplification of Nucleic Acids in Biological Samples Stored in Presence of Heterogeneous Micelles [Average RLU]

|  | C. trachomatis positive pool in 0.3% LLS |
|---|---|
| No target | 1600 |
| 0.5 fg C. trachomatis rRNA | 2,000,000 |
| 5.0 fg C. trachomatis rRNA | 1,300,000 |
| Sample in 6.4% Tween-80 | 150,000 |
| Sample in 6.0% Tween-80 | 2,400,000 |
| Sample in 7.2% Tween-80 | 2,300,000 |
| Sample in 7.6% Tween-80 | 2,800,000 |
| Sample in 8.0% Tween-80 | 2,900,000 |
| Sample in 10% Tween-80 | 3,000,000 |
| Sample in 12% Tween-80 | 2,900,000 |

EXAMPLE 9

This example illustrates the effectiveness of the method of the present invention to prevent the inhibition of enzyme-mediated reactions by ionic detergents in systems other than nucleic acid amplification reactions. Five micrograms of plasmid pUC19 (Bethesda Research Laboratories, Gaithersburg, Md.) were digested with restriction endonuclease Eco R1 at its sole Eco R1 site in a reaction mixture containing 5 μl of 10× High Salt buffer (10 mM NaCl, 50 mM Tris (pH 7.5), 10 mM MgCl$_2$ and 1 mM DTT), 48 units of Eco R1 (48 units/μl) in a final reaction volume of 50 μl. The reaction mixture was incubated at 37° C. for 1 hour. The sample was then precipitated with a solution containing 300 μl of ethanol, 5 μl of 3M sodium acetate, and 1 μl of glycogen and redissolved in 16 μl water.

Following linearization of the circular plasmid, the plasmid was radiolabeled with [α]-$^{32}$P DATP using the Klenow fragment of *E. coli* DNA polymerase I as follows. The dissolved DNA was given 2 μl of High Salt buffer, 1 μl of [α]-$^{32}$P dATP, and 1 μl of the Klenow fragment (5 units/μl) (Stratagene, San Diego, Calif.). The reaction mixture was incubated for 20 minutes at room temperature, then precipitated by adding 2 μl of 3M sodium acetate and 200 μl ethanol, and pelleted in a microcentrifuge. The DNA was redissolved in 100 µl of water.

To test whether the addition of Tween-20 to a solution containing SDS and the radiolabeled DNA would prevent inhibition of digestion of the linearized DNA by restriction endonuclease Pvu II, different reaction mixtures were made up with varying amounts of the two detergents, as shown below. Each reaction was in a total volume of 50 µl. SDS and Tween-20 were added to the reaction mixture prior to the addition of the radiolabeled DNA. 5 microliters of 10× REACT buffer (500 mM Tris-HCl (pH 7.4), 60 mM MgCl$_2$, 500 mM NaCl, and 500 mM KCl) were also added to the reaction mixture. Ten units of Pvu II (10 units/µl) were then added to each tube, along with 1 µl (50 ng) of the radiolabeled DNA. The reaction mixture was incubated at 37° C. for 1 hour. Five microliters of each digestion mixture was added to 10 µl of non-denaturing gel loading buffer and 5 µl of water, and an aliquot of each sample was analyzed on a 7% polyacrylamide non-denaturing gel. Molecular weight markers were radiolabeled φX174 DNA digested with Hinf I. The gel was run until the running dye had reached the bottom of the gel, and the gel was used to expose X-ray film for either 4 hours or overnight. The X-ray film was exposed (FIG. 1), and the results were analyzed.

| PERCENT SDS IN EACH SAMPLE | | |
|---|---|---|
| Gel Lanes | Percent SDS | Microliters 2% SDS Solution |
| 1–5 | 0 | 0 |
| 6–10 | 0.01 | 2.5 (10 X dilution) |
| 11–15 | 0.05 | 1.25 |
| 16–20 | 0.1 | 2.5 |
| 21–25 | 0.5 | 12.5 |

| PERCENT TWEEN-20 IN EACH SAMPLE | | |
|---|---|---|
| Gel Lane | Percent Tween-20 | Microliters 50% (v/v) Tween-20 |
| 1,6,11,16,21 | 0 | 0 |
| 2,7,12,17,22 | 10 | 10 |
| 3,8,13,18,23 | 14 | 14 |
| 4,9,14,19,24 | 18 | 18 |
| 5,10,15,20,25 | 20 | 20 |

The gel lanes are numbered from left to right. The two leftmost lanes are the molecular weight markers, with their sizes (in number of bases) indicated next to the bands in the overnight exposure, followed by a negative control of Pvu II undigested, Eco R1 linearized pUC19 DNA. The lane to the far right also contains the molecular weight markers.

The Eco R1 site in the 2686 bp pUC19 plasmid is at map position 396. The Pvu II sites in pUC19 are at map positions 306 and 628. Thus, a complete digestion of the pUC19 DNA would yield expected fragments of 90, 232, and 2364 bp in length.

The results, shown in FIG. 1, indicate that Pvu II digestion is inhibited by concentrations of SDS as low as 0.01% (w/v). However, the addition of 10–20% Tween-20 to the reaction mixture before addition of the enzyme allows the restriction digestion to occur.

The foregoing examples demonstrate currently preferred embodiments of the present invention. However, it will be immediately appreciated by those skilled in the art in light of this disclosure that other combinations of enzymes, ionic detergents and non-ionic detergents may be used in the method of the present invention. Other such combinations may be screened for use in the present invention without undue experimentation using the methods disclosed herein in conjunction with standard enzyme assay procedures.

What is claimed is:

1. A kit for amplifying a target nucleic acid, comprising:
 a) a first reagent comprising at least one ionic detergent;
 b) a second reagent comprising at least one non-ionic detergent for mixing with the first reagent in an amount such that after mixing said first and second reagents said at least one non-ionic detergent is present at a concentration from about 6% to about 20%,
 c) at least one nucleic acid primer able to hybridize to the target nucleic acid sequence, and
 d) at least one enzyme having nucleic acid polymerase activity for initiating the nucleic acid amplification reaction.

2. The kit of claim 1 wherein said at least one non-ionic detergent is selected from the group consisting of a polyoxyethylene sorbitan monoalkylate and a polyoxyethylene p-t-octyl phenol derivative.

3. The kit of claim 2 wherein said at least one non-ionic detergent is a polyoxyethylene sorbitan monolaurate.

4. The kit of claim 3 wherein said at least one enzyme is a thermostable DNA polymerase derived from *Thermus aquaticus*.

5. The kit of claim 4 wherein said at least one ionic detergent is present in an amount such that after mixing with said second reagent it has a concentration of about 0.1% to about 1.5%.

6. The kit of claim 5 wherein said at least one ionic detergent is a water soluble lauryl sulfate salt.

7. The kit of claim 6 wherein said at least one ionic detergent is lithium lauryl sulfate.

8. The kit of claim 1 further comprising a protease.

9. The kit of claim 3 further comprising a protease.

10. The kit of claim 3 wherein said at least one enzyme is selected from the group consisting of a retroviral reverse transcriptase, an RNA polymerase, and a DNA polymerase derived from *Bacillus stearothermophilus*.

11. The kit of claim 10 wherein said at least one ionic detergent is present in an amount such that after mixing with said second reagent it has a concentration of about 0.1% to about 1.5%.

12. The kit of claim 11 wherein said at least one ionic detergent is a water soluble lauryl sulfate salt.

13. The kit of claim 12 wherein said at least one ionic detergent is lithium lauryl sulfate.

14. The kit of claim 10 further comprising a protease.

15. The kit of claim 2 wherein said at least one non-ionic detergent is selected from the group consisting of a polyoxyethylene sorbitan monooleate, a polyoxyethylene sorbitan monopalmitate, and a polyoxyethylene p-t-octyl phenol derivative.

16. The kit of claim 13 wherein said at least one enzyme is a thermostable DNA polymerase derived from *Thermus aquaticus*.

17. The kit of claim 16 wherein said at least one ionic detergent is present in an amount such that after mixing with said second reagent it has a concentration of about 0.1% to about 1.5%.

18. The kit of claim 17 wherein said at least one ionic detergent is a water soluble lauryl sulfate salt.

19. The kit of claim 18 wherein said at least one ionic detergent is lithium lauryl sulfate.

20. The kit of claim 16 further comprising a protease.

21. The kit of claim 15 wherein said at least one enzyme is selected from the group consisting of a retroviral reverse transcriptase, an RNA polymerase, and a DNA polymerase derived from *Bacillus stearothermophilus*.

22. The kit of claim 21 wherein said at least one ionic detergent is present in an amount such that after mixing with said second reagent it has a concentration of about 0.1% to about 1.5%.

23. The kit of claim 22 wherein said at least one ionic detergent is a water soluble lauryl sulfate salt.

24. The kit of claim 23 wherein said at least one ionic detergent is lithium lauryl sulfate.

25. The kit of claim 21 further comprising a protease.

* * * * *

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
( A ) LENGTH: 53
( B ) TYPE: nucleic acid
( C ) STRANDEDNESS: single
( D ) TOPOLOGY: linear ( i i ) SEQUENCE DESCRIPTION: SEQ ID NO: 1:

AATTTAATAC GACTCACTAT AGGGAGAGCG TAGCGATGAC CTATTTACT TGC    53

( 2 ) INFORMATION FOR SEQ ID NO: 2:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 2:

TGTAGTGATC ATATCAGAGT GG    22

( 2 ) INFORMATION FOR SEQ ID NO: 3:

( i ) SEQUENCE CHARACTERISTICS:
        ( A ) LENGTH: 36
        ( B ) TYPE: nucleic acid
        ( C ) STRANDEDNESS: single
        ( D ) TOPOLOGY: linear ( i i ) SEQUENCE DESCRIPTION: SEQ ID NO: 3:

GTGATCATAT CAGAGTGGAA ATACCTGTTC CCATCC     36

( 2 ) INFORMATION FOR SEQ ID NO: 4:

( i ) SEQUENCE CHARACTERISTICS:
        ( A ) LENGTH: 30
        ( B ) TYPE: nucleic acid
        ( C ) STRANDEDNESS: single
        ( D ) TOPOLOGY: linear ( i i ) SEQUENCE DESCRIPTION: SEQ ID NO: 4:

GCTTGTGTCT TCAGTTCGTG AGATCTCGGC     30

( 2 ) INFORMATION FOR SEQ ID NO: 5:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) SEQUENCE DESCRIPTION: SEQ ID NO: 5:

GCAATGTAGG TGTATCTCC     19

( 2 ) INFORMATION FOR SEQ ID NO: 6:

( i ) SEQUENCE CHARACTERISTICS:
        ( A ) LENGTH: 16
        ( B ) TYPE: nucleic acid
        ( C ) STRANDEDNESS: single
        ( D ) TOPOLOGY: linear ( i i ) SEQUENCE DESCRIPTION: SEQ ID NO: 6:

TATGCACAGA GCTGCA     16

( 2 ) INFORMATION FOR SEQ ID NO: 7:

( i ) SEQUENCE CHARACTERISTICS:
        ( A ) LENGTH: 28
        ( B ) TYPE: nucleic acid
        ( C ) STRANDEDNESS: single
        ( D ) TOPOLOGY: linear ( i i ) SEQUENCE DESCRIPTION: SEQ ID NO: 7:

GAACAGCAAT ACAACAAACC GTTGTGTG     28

( 2 ) INFORMATION FOR SEQ ID NO: 8:

( i ) SEQUENCE CHARACTERISTICS:
        ( A ) LENGTH: 49
        ( B ) TYPE: nucleic acid
        ( C ) STRANDEDNESS: single
        ( D ) TOPOLOGY: linear ( i i ) SEQUENCE DESCRIPTION: SEQ ID NO: 8:

AATTTAATAC GACTCACTAT AGGGAGACCC GAAGATTCCC CTTGATCGC     49

( 2 ) INFORMATION FOR SEQ ID NO: 9:

( i ) SEQUENCE CHARACTERISTICS:
( A ) LENGTH: 33
( B ) TYPE: nucleic acid
( C ) STRANDEDNESS: single
( D ) TOPOLOGY: linear ( i i ) SEQUENCE DESCRIPTION: SEQ ID NO: 9:

CGGAGTAAGT TAAGCACGCG GACGATTGGA AGA    33

( 2 ) INFORMATION FOR SEQ ID NO: 10:

( i ) SEQUENCE CHARACTERISTICS:
( A ) LENGTH: 24
( B ) TYPE: nucleic acid
( C ) STRANDEDNESS: single
( D ) TOPOLOGY: linear ( i i ) SEQUENCE DESCRIPTION: SEQ ID NO: 10:

AGAGTCCGTA GAGCGATGAG AACG    24